(12) United States Patent
Sherpa et al.

(10) Patent No.: US 10,424,035 B1
(45) Date of Patent: Sep. 24, 2019

(54) MONITORING CONDITIONS ASSOCIATED WITH REMOTE INDIVIDUALS OVER A DATA COMMUNICATION NETWORK AND AUTOMATICALLY NOTIFYING RESPONSIVE TO DETECTING CUSTOMIZED EMERGENCY CONDITIONS

(71) Applicants: Trungram Gyaltrul R. Sherpa, Cambridge, MA (US); David H. C. Chen, Palo Alto, CA (US)

(72) Inventors: Trungram Gyaltrul R. Sherpa, Cambridge, MA (US); David H. C. Chen, Palo Alto, CA (US)

( * ) Notice: Subject to any disclaimer, the term of this patent is extended or adjusted under 35 U.S.C. 154(b) by 0 days.

(21) Appl. No.: 15/981,885

(22) Filed: May 16, 2018

(51) Int. Cl.
    *G06Q 50/26*    (2012.01)
    *G06F 11/30*    (2006.01)
    *G06F 11/34*    (2006.01)
    *G06N 20/00*    (2019.01)

(52) U.S. Cl.
    CPC ....... *G06Q 50/265* (2013.01); *G06F 11/3006* (2013.01); *G06F 11/3438* (2013.01); *G06N 20/00* (2019.01)

(58) Field of Classification Search
    CPC ..... G06F 19/30; G08B 21/02; G08B 21/0446; G08B 21/0453
    USPC .............................. 340/539.11–539.14, 573.1
    See application file for complete search history.

(56) References Cited

U.S. PATENT DOCUMENTS

| | | | |
|---|---|---|---|
| 9,019,100 B2 * | 4/2015 | Sholder | G08B 21/02 340/539.13 |
| 9,186,105 B2 * | 11/2015 | Leininger | A61B 5/0488 |
| 9,257,029 B1 * | 2/2016 | Hendrick, III | G08B 21/0415 |
| 9,361,778 B1 * | 6/2016 | German | G08B 21/0423 |
| 9,848,780 B1 * | 12/2017 | DeBusschere | A61B 5/0082 |
| 9,940,822 B2 * | 4/2018 | Sella | G08B 21/0423 |
| 10,026,292 B2 * | 7/2018 | Baker | G08B 21/0446 |
| 2008/0001735 A1 * | 1/2008 | Tran | G06F 19/3418 340/539.22 |
| 2012/0220835 A1 * | 8/2012 | Chung | A61B 5/0022 600/301 |
| 2016/0071390 A1 * | 3/2016 | Sales | A61B 5/1114 340/573.1 |
| 2016/0260310 A1 * | 9/2016 | Chuang | G08B 21/0446 |

* cited by examiner

*Primary Examiner* — Eric Blount
(74) *Attorney, Agent, or Firm* — Schwegman Lundberg & Woessner, P.A.

(57) ABSTRACT

Individuals are remotely monitored over a data communication network to automatically detect and responds to anomalous conditions. A user account of a plurality of user accounts is configured for remote monitoring for emergency conditions of monitored individuals. A monitoring device can be wearable and in physical contact with a first individual. A notifying device can also be wearable for a second individual for notification of emergency conditions. An anomalous condition is detected. The monitoring device includes sensors that measure conditions within and around the first individual, and send readings to the anomalous condition server for analysis. An alert is sent responsive to the anomaly determination, from the network communication interface, to the notifying device, according to personalized settings of the second individual.

20 Claims, 5 Drawing Sheets

MONITORING CONDITIONS ASSOCIATED WITH REMOTE INDIVIDUALS OVER A DATA COMMUNICATION NETWORK AND AUTOMATICALLY NOTIFYING RESPONSIVE TO DETECTING CUSTOMIZED EMERGENCY CONDITIONS

FIELD OF THE INVENTION

The present invention relates generally to computer systems and networking, and more specifically to, computer systems to monitor conditions associated with remote individuals over a data communication network and automatically notify if customized emergency conditions are detected.

BACKGROUND

Various monitoring systems are available to monitor loved ones, such as video monitoring or alert bracelets. A video monitoring system allows a relative to view video cameras over a network. One or more cameras can be set up to cover limited areas of a household. Typical alert bracelets are worn on the body and notify an emergency service, for example, after a fall. Both techniques rely upon active participation by either the relative or the individual.

Not only to these conventional systems involve extensive human interaction for monitoring, the human also has to correctly assess a situation remotely and this could be difficult in subtle situations, such as stroke. The video system, however, is just video and audio.

Furthermore, the current network architectures are devoid of monitoring in a manner that is specific to an individual. Nor is there provided notification in a manner that is specific to a relative of the individual.

What is desired is a technique for automatically monitoring conditions associated with remote individuals over a computer network. Furthermore, the technique should automatically detect and notify customized emergency conditions.

SUMMARY

The above-described shortcomings are resolved by a system, method, and source code for remotely monitoring an individual over a data communication network to automatically detect and respond to anomalous conditions.

In one embodiment, a user account of a plurality of user accounts is configured for remote monitoring for emergency conditions of monitored individuals. A monitoring device can be wearable and in physical contact with a first individual. A notifying device can also be wearable for a second individual for notification of emergency conditions. Both monitoring and notifying devices can be registered with an anomalous condition server over a data communications network.

In another embodiment, an anomalous condition is detected. The monitoring device comprises sensors that measure conditions within and around the first individual, and send readings to the anomalous condition server for analysis. Various types of analysis comprise comparison against a threshold, known signature identification, pattern recognition, machine learning classification, artificial intelligence (AI) prediction, unsupervised learning, or a combination thereof. By doing so, the system may determine an anomaly which can be either known or unknown at the time of deployment, for future-proof utilizations.

An alert is sent responsive to the anomaly determination, from the network communication interface, to the notifying device, according to personalized settings of the second individual.

Advantageously, loved ones can be easily monitored for emergency conditions. This emergency monitoring system technologies improve emergency notification system technologies.

BRIEF DESCRIPTION OF THE DRAWINGS

In the following drawings, like reference numbers are used to refer to like elements. Although the following figures depict various examples of the invention, the invention is not limited to the examples depicted in the figures.

DETAILED DESCRIPTION

The following description presents systems, methods, and source code (e.g., non-transitory source code stored on a computer-readable medium for execution by a processor) for remotely monitoring an individual over a data communication network to automatically detect and respond to anomalous conditions, such as an emergency.

Generally, anomalous conditions refer to various internal body states and/or various surrounding external or environmental factors that could negatively affect the body states (e.g., emergency condition of a loved one). Examples of internal body states include medical, physiological, mental, non-medical, and the like. Examples of external factors include the environment, ambient temperature, humidity, noise levels, gas levels, and the like. In one embodiment, condition monitoring is specific to an individual being monitored and notifications are specific to an individual being notified. In another embodiment, dynamic anomalous conditions can change based on analysis of big data trends. Anomalies can have different configurable levels of urgency ranging from minor anomalies that are merely recorded to major anomalies that rise to emergency notifications.

This description is intended to enable one of ordinary skill in the art to make and use the embodiments and is provided in the context of a patent application and its requirements. Various modifications to the preferred embodiments and the generic principles and features described herein will be readily apparent to those skilled in the art. Thus, the present embodiments are not intended to be limited as shown, but are to be accorded the widest scope consistent with the principles and features described herein.

I. Systems for Anomaly Condition Monitoring (FIGS. 1-2)

Figure 1:
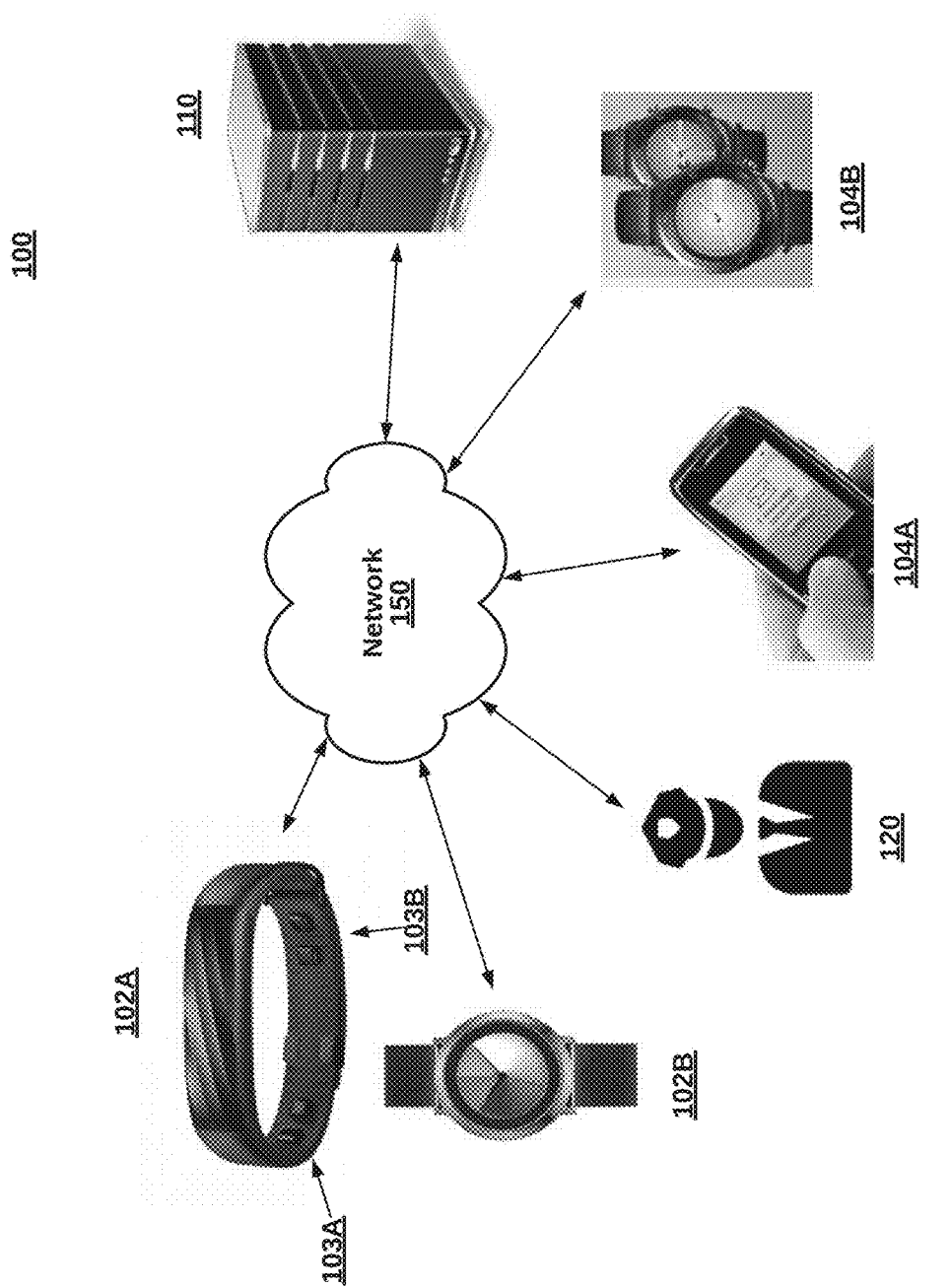
FIG. 1 is a high-level block diagram illustrating a system for monitoring and notification of anomalous conditions associated with a remote individual, according to an embodiment.
Figure 2:
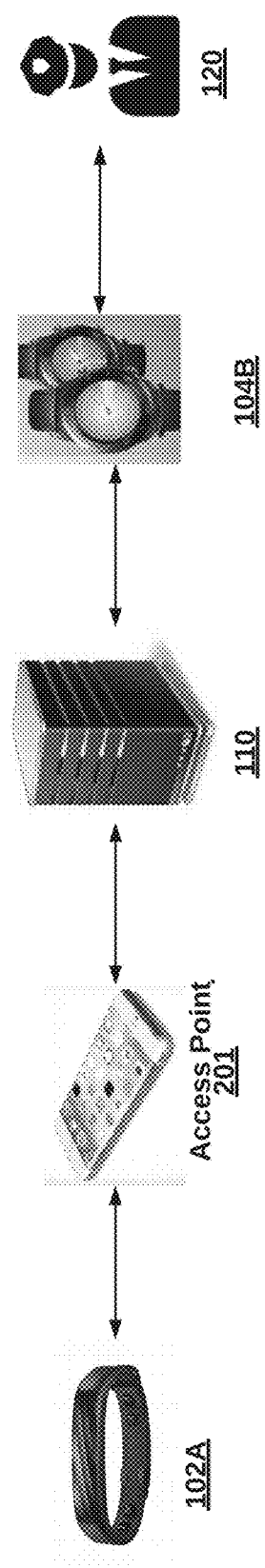
FIG. 2 is a block diagram illustrating an example data path with an access point for the system of FIG. 1, according to an embodiment.

FIG. 1 is a block diagram illustrating a system 100 for dynamic monitoring and notification of anomalous conditions associated with a remote individual, according to an embodiment. The system 100 comprises a monitoring devices 102A,B (generically referred to as 102), a notifying devices 104A,B (generically referred to as 104), an anomalous condition server 110 and external resources 120 connected to a network 150. Many other configurations are possible. The components can be implemented in hardware, software, or a combination of both (e.g., see computing environment FIG. 6).

The network 150 can be the Internet, a wide area network, a local area network, a cellular network (e.g., 3G or 4G), a hybrid network, or the like to transmit data packets between a transmitter and a receiver. Additional network infrastructure devices are not shown such as access points, routers, switches, and the like. The monitoring device 102 and the notifying device 104 can be wirelessly coupled to the network 150 over a Wi-Fi channel or other wireless communication mechanism. The anomalous condition server 110 is preferably coupled to the network 150 over an Ethernet or other wired communication mechanism. The optional external resources 120 can be wired or wireless. In one example, wireless devices are configured with hardware and software to transmit and receive packets formatted according to IEEE 802.11 or another communication protocol. In another example, wired devices are configured with hardware and software to transmit and receive packets formatted according to IEEE 802.3 or another communication protocol.

The anomalous condition server 110 can detect emergency conditions associated with the monitoring device 102 and alert the notifying device 104, in an embodiment. In one case, biomedical sensors and physiological response sensors can be embedded within the monitoring device 102, attached thereto, or be wirelessly connected. If a blood pressure level or insulin level reaches a certain point, a relative, friend, physician or paramedics can be notified. In another case, biomedical sensor readings in combination with an ambient temperature and an individual's age are all factors that make an emergency situation for that individual. In still another case, carbon monoxide environmental conditions sensed by a third device that, although unrelated to the monitoring device and the notifying device, affects the individual's condition. In more detail, the third device can be part of big data trends, or part of a group of nearby devices associated with strangers to the monitored individual and to the notified individual. Many other examples provide additional categories and further detail these general categories herein.

To detect anomalous conditions, the anomalous condition server 110 actively retrieves and analyzes data from various sources in determining when to notify the notifying device 104, in an embodiment. Additionally, external resources 120 can be accessed to determine whether threshold levels should be dynamically adjusted based on updated big data trends, prescriptions, inventory levels, other information publicly available on the Internet, or the like.

Optionally, a location of the anomaly origin is determined. For example, an anomaly of a loud sound can be caused by gunfire. Machine/deep learning classification process may identify the gunfire by performing a windowed scan on the sound and classifying each window (using decision tree classifiers). Trilateration or other process can point out the location of the gunfire based on GPS locations of the monitoring device 102 which capture the sound. The system 100 informs police or other authorities with access to a computational device connected to the network 150. This will help the authority quickly response to the gunfire location by notifying a police server within the external resources 120. Location can also be important in detecting outbreaks of influenza or other diseases, for example, by identifying high body/skin temperatures within a certain GPS-located area.

The anomalous condition server 110 can be utilized and controlled by a single entity. Many entities or users can subscribe to a service provided to the public. The foregoing gunfire trilateration and influenza isolation may be parts of the service provided with the anomalous condition server 110. Various embodiments of the anomalous condition server are described in more detail below with respect to FIG. 3.

As one of the inputs, the monitoring device 102 reports local information from sensors to the anomalous condition server 110. Examples of the monitoring device 102 in FIG. 1 is shown as a bracelet 102A and a watch 102B. One or more sensors 103A,B collect data locally to send upstream for analysis against previous data, user thresholds, aggregate trends, or big data findings in the aggregate based on monitoring of other individuals. Processing loads can be shared between the monitoring device 102 and the anomaly condition server 110. Local processes can include pre-processing, filtering, data formatting, data averaging over a window of time, and the like. A cloud-heavy processing distribution allows smaller form factors and more subtle, lightweight devices. Responsive to an anomaly condition rising to the level of an emergency can result in a color change by the watch 102B or a vibration or audible alert by the bracelet 102A.

The monitoring device 102 can have integrated sensors, packaged or otherwise enclosed inside an enclosure, to appear as a single product like a ring, bracelet, wristband, earplug, earphone, watch, smart glasses, smart wearable, or other product. An embodiment may deploy flexible electronics technologies, such as polyimide or conductive polyester substrate(s), for assembling a wristband or other bendable products. Alternatively, the sensors can be detachably mounted or plugged into the monitoring device 102, or be wirelessly connected. Software applications can be downloaded and installed for general monitoring or for monitoring a specific condition.

Additional embodiments of the monitoring device 102 is set forth in more specificity below in association with FIG. 4.

The notifying device 104 can display alerts locally to an individual in emergency or less urgent situations, according to settings. Embodiments of the notifying device 104 may deploy e-ink, e-paper, LCD, LED or touchscreen display to change display color, to show text message, email, badge, banner, alert, visible object, or a combination thereof. When the notifying device 104B is unavailable (or does not acknowledge an alert), notifications could be presented by a smartphone 104A. In some embodiments, a person may configure a user account to predetermine a list of recipients to receive the notification when anomalies occur. The list of recipients may comprise the person, a love one, a first responder, or a combination thereof. The person may also predetermine a list of contents to be included in a notification. The content list may comprise the person's identity, cellphone number, contact information, location, the measurement, raw data, or a combination thereof.

Parameters allow the loved ones or other monitoring individuals to accept or to refuse notifications. The recipients may predetermine how notifications should be presented by customizing notification parameters. A notification could be presented as a color change, sound, alarm, voice, phone call, vibration, text message, email, badge, banner, alert, visible object, raw data, or a combination thereof. If a recipient permits any of such notifications, the recipient may take actions to comfort or to care the person upon receiving a notification. One embodiment changes the notifying device 104 back to a default state when the emergency has subsided. For example, a notification can be sent out to two different watches 104B and the first watch to indicate the responsibility for the alert has been accepted, results in ending the notification for the other watch, and optionally the monitoring device 102 can also indicate that help is on the way. In one embodiment, the external resources 120 is notified. Software applications can be downloaded and installed for general notifications or for notifying for a specific condition.

FIG. 2 is a block diagram illustrating a data path including an access point, according to an embodiment. A smart phone is shown as an access point to the network 150. Processing loads are performed by the monitoring device 102. Many other data paths are possible. For example, there can be multiple access points configured in a mesh network.

Figure 3:
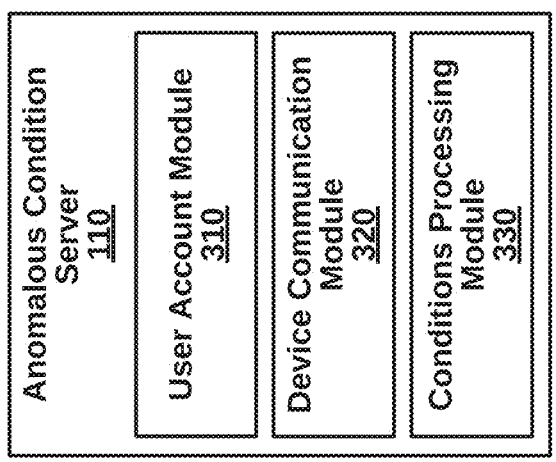
FIG. 3 is a more detailed block diagram illustrating an anomalous condition server of the system of FIG. 1, according to an embodiment.

FIG. 3 is a block diagram illustrating the anomalous condition server 110 of the system of FIG. 1, according to an embodiment. The anomalous condition server 110 comprises a user account module 310, a device communication module 320 and a conditions processing module 330. Many other components are not shown. One embodiment comprises hardware and software interaction as discussed below concerning FIG. 6.

The use account module 310 can be a database of all individuals being monitored. Each can have a login to securely configure parameters and store data from monitoring device 102. Furthermore, login credentials can be stored for an external resource 120 such as a login info for a pharmacy server. The device communication module 320 can register devices associated with individuals being monitored and devices associated with individuals being notified.

To detect anomalous conditions, the conditions processing module 330 retrieves data from various sources in determining when to notify the notifying device 104, in an embodiment. One type of analysis compares a measurement received as data, to an average or a range/limit determined by prior measurements, or compares the measurement to a predetermined safe range. For example, threshold comparison may compare a detected extreme brightness to a predetermined threshold to identify an explosion. In another example, the average or range/limit can be a variable depending on time, day, date, other variables or a combination thereof. For example, a heartrate range/limit can be a variable depending on whether the person is exercising or not.

One type of analysis recognizes anomaly using voice recognition. For example, a voice calling for help can be recognized as an anomaly. Another type of analysis identifies anomaly with its signature or pattern. Signature identification may identify pain using a detected heartrate change as a known signature. Pattern recognition, such as geometric data analysis, may analyze a detected dialogue and reveal emotions of a speaker. Still another type of analysis classifies (with machine/deep learning or artificial intelligence algorithms) the measurement. Still another type of analysis makes predications with deep learning or artificial intelligence (AI). For example, deep learning or AI may be pretrained with retrospective patient's intracranial electroencephalography (iEEG) data, and predict epilepsy of seizures to allow preventative treatment.

Still another type of analysis uses unsupervised learning to determine unknown anomalies as they stand in contrast to an established baseline condition. The baseline condition may be established by ongoing profiling of database associated with a plurality of user accounts. With unsupervised learning, a processor is continuously updated to determine new medical, psychological or ambient/environmental anomalies. Still another type of analysis uses big data sources to identify trends and relative severity of the conditions for comparison against locally detected data. The conditions processing module can include a microprocessor, and one or more software processes or applications.

Figure 4:
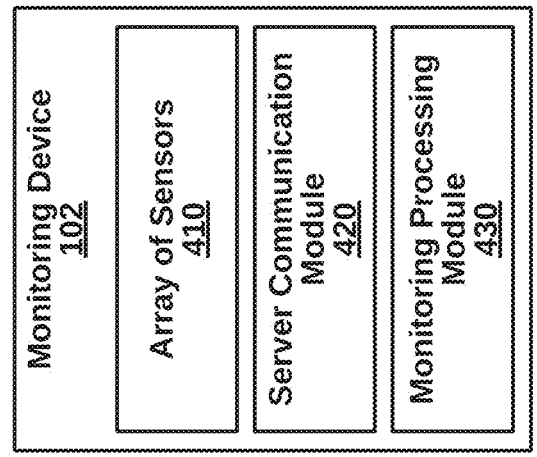
FIG. 4 is a more detailed block diagram illustrating a monitoring device of the system of FIG. 1, according to an embodiment.

FIG. 4 is block diagram illustrating an example monitoring device 102 of the system of FIG. 1, according to an embodiment. The monitoring device comprises an array of sensors 410, a server communication module 420 and a monitoring processing module 430. Additional hardware and software implementations are discussed below in relation to FIG. 6.

The array of sensors 410 can measure local physiological response or biochemical activity for vital sign monitoring. For example, pulse oximeter may monitor the oxygen saturation of arterial blood (SpO2), produce a photoplethysmogram (PPG), and identify respiratory diseases or other medical conditions. Since heartrate variation, cutaneous blood flow, and sweating can accompany various emotions (psychological or mental states), a Holter monitor may effectively differentiate happiness, stress, sadness and neutral. Some ambient conditions such as extreme brightness and loudness may be easily detected with phototransistor and microphone respectively, to indicate an explosion. Respiratory diseases, sadness, and explosions are exemplified and nonlimiting examples of urgent events detectable with sensors.

Other sensor examples include measuring heart rate, heartbeat, heart rate variability (HRV), oxygen in the blood, blood pressure, skin temperature, body temperature, skin conductivity, galvanic skin response (GSR), electrodermal activity (EDA), psychogalvanic reflex (PGR), skin conductance response (SCR), sympathetic skin response (SSR), skin conductance level (SCL), skin moisture, motion, movement, activity level, inertial movement, ambient sound, ambient light, location, or a combination thereof. PPG sensors, pulse-oximeters or pairs of infrared (IR) LED and light-sensitive photodiode (PD) may be configured to measure heartrates, heartbeats, HRV, oxygen in the blood, or a combination thereof. Oscillometric sensors may be configured to measure blood pressures. Infrared thermometers may be configured to measure skin or body temperatures. Skin conductance sensors, galvanic resistance sensors (GRS), or 2 silver chloride (AgCl) electrodes and a voltage source may be configured to measure skin conductivity, GSR, EDA, PGR, SCR, SSR, SCL, skin moistures, or a combination thereof. Accelerometers, pedometers, gyroscopes or global positioning systems (GPS) may be configured to measure motions, movements, activity levels, inertial movements, or a combination thereof. Microphones may be configured to measure ambient sounds. Photoresistors, photodiodes or phototransistors may be configured to measure ambient lights. GPS devices may be configured to determine locations. An embodiment may deploy PCM1870 from Texas Instruments, or similar commercial products, when analog to digital conversion is necessary in order to send computer readable data.

The server communication module 420 establishes network communication between the monitoring device 102 and the anomaly detection server 110. As shown in FIG. 2, one data path is to connect the monitoring device 102A, over a Bluetooth channel or a mesh Wi-Fi channel, to a smartphone 201 as an access point. In turn, the smartphone 201 is coupled through the network 150. Alternatively, the monitoring device 102 can have an embedded 3G/4G transceiver to couple with the network 150 directly. As needed, the anomaly condition server 110 transmits through the network 150 to a first watch and a second watch of the notifying devices 104B. Finally, a loved one may optionally make a decision to notify the authorities.

The monitoring processing module 430 can include a microprocessor and software processes for local processing.

II. Methods for Anomaly Condition Monitoring (FIG. 5)

Figure 5:
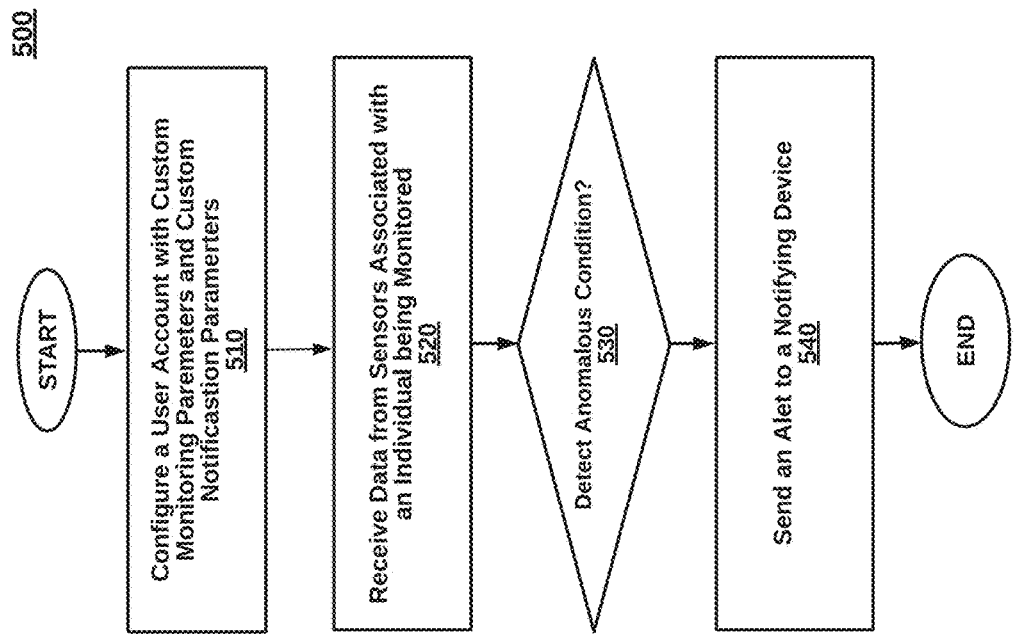
FIG. 5 is a high-level flow chart illustrating a method for monitoring and notification of anomalous conditions associated with a remote individual, according to an embodiment.

FIG. 5 is a flow chart illustrating a method 500 for monitoring and notification of anomalous conditions associated with a remote individual, according to an embodiment. The method 500 can be implemented in system 100 of FIG. 1 or others. The steps are generally groupings of functionality and can be performed in a different order, with additional steps and sub-steps.

At step 510, a user account is configured with customer monitoring and/or notification parameters. The monitoring parameters can be based on physiological responses, biochemical activities, ambient conditions, or a combination thereof. The monitoring parameters may depend on what conditions are being monitored, which sensors are being used, or other factors of an individual. Optionally, parameters can be dynamically adjusted by artificial intelligence, doctor's orders, a change in temperature, new conditions of the individual being monitored, or for other reasons.

At step 520, data is received from sensors associated with an individual being monitored. A communications interface coupled to a network receives data for processing.

At step 530, it is determined whether an anomalous condition has occurred. In such exemplified embodiment, the step 530 would be comparing the measured sound to a predetermined amplitude or threshold, classifying the sound, performing pattern recognition with conventional approaches, neural networks or artificial intelligence (AI) algorithms, or conducting a combination thereof.

Responsive to detecting an anomalous condition, at step 540, an alert is sent to a notifying device. The notification could help loved ones to quickly extend assistance to the individual being monitored.

III. Generic Computing Environment (FIG. 6)

Figure 6:
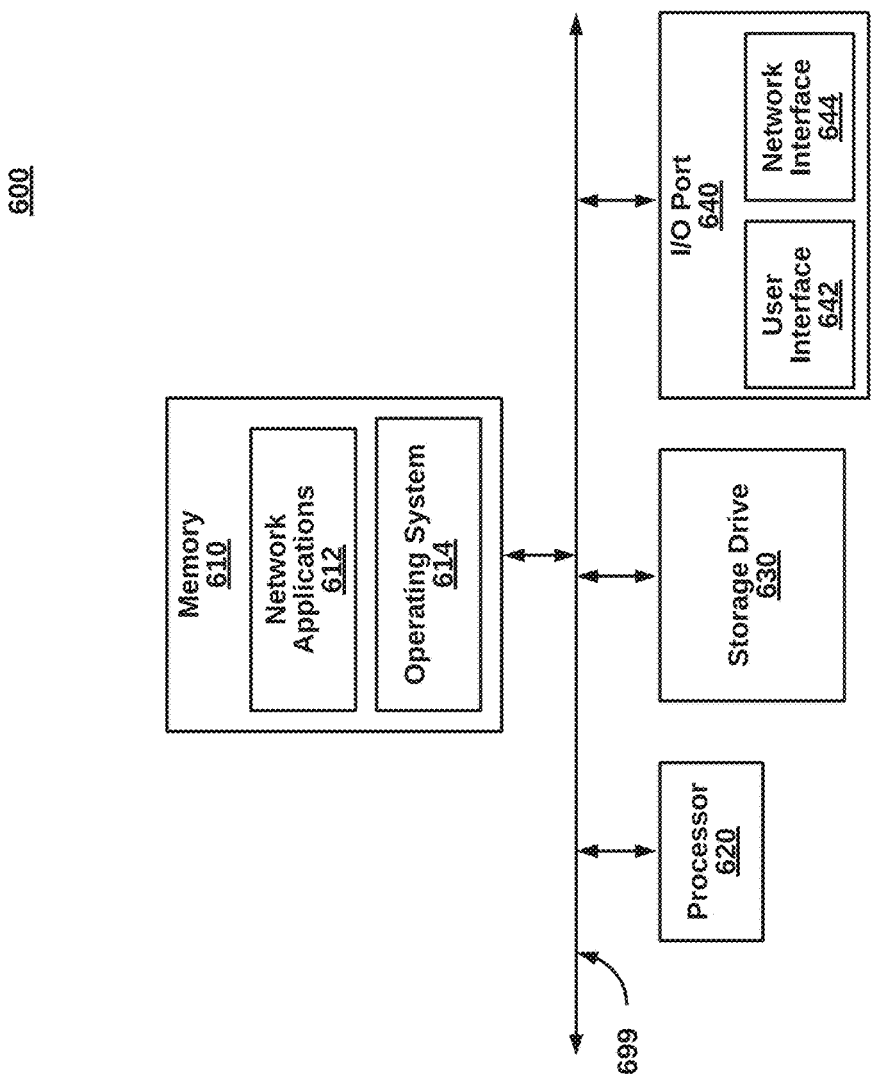
FIG. 6 is a block diagram illustrating a computing environment capable of implementing the system of FIG. 1 and method of FIG. 5, according to an embodiment.

FIG. 6 is a block diagram illustrating an exemplary computing device 600 for use in the system 100 of FIG. 1, according to one embodiment. The computing device 600 is an exemplary device that can be implemented as a monitoring device 102, a notifying device 104 or an anomalous condition server 110. In one embodiment, the same computing device 600 is implemented as both a monitoring device and a notifying device. Such that, the monitoring device can also receive an alert responsive to an anomaly detected by itself or by another monitoring device.

Additionally, the computing device 600 is merely an example implementation itself, since the system 100 can also be fully or partially implemented with laptop computers, tablet computers, smart cell phones, Internet appliances, and the like.

The computing device 600, of the present embodiment, includes a memory 610, a processor 620, a storage drive 630, and an I/O port 640. Each of the components is coupled for electronic communication via a bus 699. Communication can be digital and/or analog, and use any suitable protocol.

The memory 610 further comprises network applications 612 and an operating system 614. The network applications 612 can include a web browser, a mobile application, an application that uses networking, a remote application executing locally, a network protocol application, a network management application, a network routing application, or the like.

The operating system 614 can be a real-time operating system (RTOS). To serve the foregoing processes and applications as soon as the data come in with deterministic delays, an embodiment may deploy one of the following RTOS: Apache Mynewt, uKOS, Atomthreads, BOOS Cores, BRTOS, CapROS, cocoOS, Contiki, distortos, eChronos, Embox, Embkernel, Femto OS, FreeOSEK, FreeRTOS, Frosted, Helium, IntrOS, ISIX, iRTOS, KolibriOS, Lepton, MaRTE OS, mbed-rtos, Milos, miosix, nOS, Nut/OS, NuttX, OSA, Pharos, POK, RIOT, RODOS, RT-Thread, scmRTOS, SDPOS, silRTOS, StateOS, TizenRT, Tock OS, TNKernel, TNeo, Y@SOS, MontaVista Linux, uOS, and Zephyr. Other operating systems may be used.

The processor 620 can be a microcontroller unit (MCU), application processor (AP), central processing unit (CPU), floating point unit (FPU), digital signal processor (DSP), system on a chip (SoC), other computational hardware, or a combination thereof. An embodiment may deploy STM32 from STMicroelectronics, or similar commercial products, as a microcontroller unit (MCU). The processor 620 can be single core, multiple core, or include more than one processing elements. The processor 620 can be disposed on silicon or any other suitable material. The processor 620 can receive and execute instructions and data stored in the memory 610 or the storage device 630.

The storage device 630 can be any non-volatile type of storage such as a magnetic disc, EEPROM, Flash, or the like. The storage device 630 stores code and data for applications.

The I/O port 640 further comprises a user interface 642 and a network interface 644. The account holder interface 642 can output to a display device and receive input from, for example, a touchscreen. The network interface 644 connects to a medium such as Ethernet or Wi-Fi for data input and output. In one embodiment, the network interface 644 includes IEEE 802.11 antennae.

Many of the functionalities described herein can be implemented with computer software, computer hardware, or a combination.

Computer software products (e.g., non-transitory computer products storing source code) may be written in any of various suitable programming languages, such as C, C++, C#, Java, JavaScript, PHP, Python, Perl, Ruby, and AJAX. The computer software product may be an independent application with data input and data display modules. Alternatively, the computer software products may be classes that are instantiated as distributed objects. The computer software products may also be component software such as Java Beans (from Sun Microsystems) or Enterprise Java Beans (EJB from Sun Microsystems).

Furthermore, the computer that is running the previously mentioned computer software may be connected to the network 150 and may interface to other computers using this network 150. The network may be a wired network (e.g., using copper), telephone network, packet network, an optical network (e.g., using optical fiber), or a wireless network, or any combination of these. For example, data and other information may be passed between the computer and components (or steps) of a system of the invention using a wireless network using a protocol such as Wi-Fi (IEEE standards 802.11, 802.11a, 802.11b, 802.11e, 802.11g, 802.11i, 802.11n, and 802.ac, just to name a few examples). For example, signals from a computer may be transferred, at least in part, wirelessly to components or other computers.

In an embodiment, with a Web browser executing on a computer, a user accesses a system on the World Wide Web (WWW) through a network such as the Internet. The Web browser is used to download web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the present invention.

What is claimed is:

1. A computer-implemented method in an anomaly server on a data communication network and implemented at least partially in hardware, the method for real-time remote detection of anomaly psychological or biochemical conditions within or around individuals being monitored and comprising:
    configuring a user database of the anomaly condition server for a specific user account of a plurality of user accounts for remote monitoring for urgent psychological or biochemical conditions of a first individual, including registering a monitoring, device being wearable and in physical contact with the first individual to measure psychological or biochemical data internal to the first individual, and registering a notifying device associated with a second individual, wherein both the monitoring device and the notifying device are coupled in communication with the anomaly server over the data communication network;
    determining, based on sensor data gathered from monitoring devices registered to the plurality of user accounts, an expected baseline condition of the first individual;
    receiving, at a network communication interface of the anomaly condition server, data concerning the first individual, the data sourced by at least one sensor of the monitoring device;
    determining, by the anomaly condition server, a current condition of the first individual based on the data received from the monitoring device;
    comparing the current condition of the first individual to the expected baseline condition of the first individual, yielding a comparison;
    determining by a processor of the anomaly condition server and based on the comparison, that the current condition of the first individual amounts to an anomalous psychological or biochemical condition with respect to the first individual, yielding an anomaly determination; and
    sending, from the network communication interface to the notifying device associated with the second individual, a first alert responsive to the anomaly determination, the first alert indicating the current state of the first individual amounts to an anomalous psychological or biochemical condition.

2. The computer-implemented method of claim 1, further comprising a:
    sending, from the network communication interface to the monitoring device, a second alert responsive to the anomaly determination.

3. The computer-implemented method of claim 1, further comprising a:
    sending, to an authority associated with a first-responder, a third alert responsive to the anomaly determination.

4. The computer-implemented method of claim 1, wherein the data received from the monitoring device pertains to a medical condition of the first individual, an ambient or environmental condition surrounding the first individual, or a combination thereof.

5. The computer-implemented method of claim 1, further comprising:
    responsive to receiving data concerning the first individual, querying an external resource for related information,
    wherein the anomaly condition determination is based at least part on results of querying the external resource for related information.

6. The computer-implemented method of claim 1, wherein the first alert causes the notifying device to show a text, change a display color, create a vibration, generate a sound, or a combination thereof.

7. The computer-implemented method of claim 1, wherein the at least one sensor comprises a physiological sensor sending computer readable data by converting physiological or biochemical events associated with the first individual.

8. The computer-implemented method of claim 1, wherein the at least one sensor comprises an ambient sensor sending computer readable data by converting ambient condition events surrounding the first individual.

9. The computer-implemented method of claim 1, wherein the first alert causes a change to a display color of the notifying device.

10. The computer-implemented method of claim 9, wherein the change to the color display of the monitoring device is based at least in part on customized alert parameters set at the notifying device.

11. An anomaly server comprising:
    one or more computer processors; and
    one or more computer-readable mediums storing instructions that, when executed by the one or more computer processors, cause the anomaly server to perform operations comprising:
        configuring a user database for a specific user account of a plurality of user accounts for remote monitoring for urgent psychological and/or biochemical conditions of a first individual, including registering a monitoring device being wearable and in physical contact with the first individual to measure psychological or biochemical data internal to the first individual, and registering a notifying device associated with a second individual, wherein both the monitoring device and the notifying device are coupled in communication with the anomaly server over a data communication network;

determining, based on sensor data gathered from monitoring devices registered to the plurality of user accounts, an expected baseline condition of the first individual;

receiving, at a network communication interface of the anomaly condition server, data concerning the first individual, the data sourced by at least one sensor of the monitoring device;

determining a current condition of the first individual based on the data received from the monitoring device;

comparing the current condition of the first individual to the expected baseline condition of the first individual, yielding a comparison;

determining, based on the comparison, that the current condition of the first individual amounts to an anomalous psychological or biochemical condition with respect to the first individual, yielding an anomaly determination; and sending, to the notifying device associated with the second individual, a first alert responsive to the anomaly determination, the first alert indicating the current state of the first individual amounts to an anomalous psychological or biochemical condition.

12. The anomaly server of claim 11, the operations further comprising:
sending, to the monitoring device, a second alert responsive to the anomaly determination.

13. The anomaly server of claim 11, the operations further comprising:
sending, to an authority associated with a first-responder, a third alert responsive to the anomaly determination.

14. The anomaly server of claim 11, wherein the data received from the monitoring device pertains to a medical condition of the first individual, an ambient or environmental condition surrounding the first individual, or a combination thereof.

15. The anomaly server of claim 11, the operations further comprising:
responsive to receiving data concerning the first individual, querying an external resource for related information,
wherein the anomaly condition determinations based at least in part on results of querying the external resource for related information.

16. The anomaly server of claim 11, wherein the first alert causes the notifying device to show a text, change a display color, create a vibration, generate a sound, or a combination thereof.

17. The anomaly server of claim 11, wherein the at least one sensor comprises a physiological sensor sending computer readable data by converting physiological or biochemical events associated with the first individual.

18. The anomaly server of claim 11, wherein the at least one sensor comprises an ambient sensor sending computer readable data by converting ambient condition events surrounding the first individual.

19. The anomaly server of claim 11, wherein the first alert causes a change to a display color of the notifying device, and the change to the color display of the monitoring device is based at least in part on customized alert parameters set at the notifying device.

20. A non-transitory computer-readable medium storing instructions that, when executed by one or more computer processors of an anomaly server, cause the anomaly server to perform operations comprising:

configuring a user database for a specific user account of a plurality of user accounts for remote monitoring for urgent psychological or biochemical conditions of a first individual, including registering a monitoring device being wearable and in physical contact with the first individual to measure psychological or biochemical data internal to the first individual, and registering a notifying device associated with a second individual, wherein both the monitoring device and the notifying device are coupled in communication with the anomaly server over a data communication network;

determining, based on sensor data gathered from monitoring devices registered to the plurality of user accounts, an expected baseline condition of the first individual;

receiving, at a network communication interface of the anomaly condition server, data concerning the first individual, the data sourced by at least one sensor of the monitoring device;

determining a current condition of the first individual based on the data received from the monitoring device;

comparing the current condition of the first individual to the expected baseline condition of the first individual, yielding a comparison;

determining, based on the comparison, that the current condition of the first individual amounts to an anomalous psychological or biochemical condition with respect to the first individual, yielding an anomaly determination; and sending, to the notifying device associated with the second individual, a first alert responsive to the anomaly determination, the first alert indicating the current state of the first individual amounts to an anomalous psychological or biochemical condition.

* * * * *